United States Patent [19]
Mori

[11] Patent Number: 5,445,796
[45] Date of Patent: Aug. 29, 1995

[54] OXYGEN CONCENTRATION SENSOR WITH HEAT RESISTANT COATING

[75] Inventor: Rentaro Mori, Toyota, Japan

[73] Assignee: Toyota Jidosha Kabushiki Kaisha, Aichi, Japan

[21] Appl. No.: 185,010

[22] Filed: Jan. 24, 1994

[30] Foreign Application Priority Data

Feb. 10, 1993 [JP] Japan ................ 5-022690

[51] Int. Cl.$^6$ .............................. G01N 27/00
[52] U.S. Cl. ......................... 422/98; 422/90; 422/94; 204/429; 73/31.06
[58] Field of Search ............... 73/23.31, 23.32, 31.05, 73/31.06; 204/429; 422/94, 98, 90

[56] References Cited

U.S. PATENT DOCUMENTS

| | | | |
|---|---|---|---|
| 3,935,089 | 1/1976 | Togawa et al. | 204/429 |
| 4,045,178 | 8/1977 | Dkinaka et al. | 422/98 |
| 4,066,413 | 1/1978 | Segawa et al. | 422/98 |
| 4,265,930 | 5/1981 | Shinohara et al. | 204/429 X |
| 4,294,801 | 10/1981 | Segawa et al. | 422/98 |
| 4,297,192 | 10/1981 | Shinohara et al. | |
| 4,574,264 | 3/1986 | Takahashi et al. | 422/98 X |
| 4,582,657 | 4/1986 | Shibata et al. | 204/429 X |
| 4,797,194 | 1/1989 | Mase et al. | 204/429 X |
| 4,834,051 | 5/1989 | Tanaka et al. | 204/429 X |
| 4,863,583 | 9/1989 | Kurachi et al. | 204/429 X |
| 4,957,705 | 9/1990 | Uchikawa | 422/94 |
| 5,110,442 | 5/1992 | Kojima et al. | 204/429 X |
| 5,160,598 | 11/1992 | Sawada et al. | 204/429 |

FOREIGN PATENT DOCUMENTS

| | | |
|---|---|---|
| 0267764 | 1/1987 | European Pat. Off. . |
| 0331513 | 3/1989 | European Pat. Off. . |
| 0372425 | 12/1989 | European Pat. Off. . |
| 38139030A1 | 4/1988 | Germany . |
| 55-124057 | 9/1980 | Japan . |
| WO92/07253 | 4/1992 | WIPO . |
| WO92/12420 | 7/1992 | WIPO . |

Primary Examiner—James C. Housel
Assistant Examiner—Arlen Soderquist
Attorney, Agent, or Firm—Oliff & Berridge

[57] ABSTRACT

A porous alumina coating layer covering an oxide semiconductor type or solid electrolyte type oxygen concentration sensor carrys a catalyst (Pt/Rh) for accelerating equilibration reaction of an unburnt gas in exhaust gas from an automobile engine. The deterioration of the catalyst activity can be prevented by incorporating a thermal stability improving agent into the alumina coating layer.

19 Claims, 3 Drawing Sheets

OXYGEN CONCENTRATION SENSOR WITH HEAT RESISTANT COATING

BACKGROUND OF THE INVENTION

1. Field of the Invention

The present invention relates to an oxygen concentration sensor, more particularly to an oxygen concentration sensor with a modified alumina coating layer on the surface of the sensor.

2. Description of the Prior Art

Oxygen concentration sensors are used in various fields, particularly as a sensor for controlling exhaust gas from an engine in an automobile. The oxygen concentration sensors include an oxygen concentration differential cell type, utilizing zirconia ($ZrO_2$) solid electrolyte, and a resistance variation-detecting type, utilizing titania ($TiO_2$) semiconductor.

Such oxygen concentration sensors typically have a porous alumina coating layer on which a catalyst of Pt/Rh is carried. The porous alumina coating layer traps oil components and so forth and the catalyst of Pt/Rh accelerates equilibration of unburnt components such as hydrocarbons and carbon monoxide in the exhaust gas. The porous alumina coating layer is formed by sintering at about 1100° C. The catalyst is then carried on the porous alumina coating layer by dropwise applying a solution containing Pt chloride and Rh chloride to the coating layer or dipping the coating layer in the solution and heating them to reduce the Pt and Rh chlorides, by which fine Pt and Rh particles are deposited on the porous alumina coating layer.

The oxygen concentration sensors having a catalyst-carrying alumina coating layer have an excellent performance at the beginning, but the output of the sensors and the reaction speed are lowered after use for a long time.

The object of the present invention is to provide an oxygen concentration sensor which can have a normal output for a long time, or a prolonged life time.

SUMMARY OF THE INVENTION

The above and other objects of the present invention are attained by providing an oxygen concentration sensor comprising a sensor body and a porous ceramic coating layer carrying a catalyst for equilibrating an unburnt gas, the porous ceramic coating layer being formed on the surface of the sensor body, wherein said porous ceramic coating layer is made of a material formed by firing a mixture of alumina powder with 0.05 to 8% by weight of a thermal stability improving agent powder.

The thermal stability improving agent may be at least one oxide selected from the group consisting of rare earth elements oxides, $SiO_2$, MgO, BaO, CaO, $CeO_2$, $La_2O_3$ and alkali metal oxides. The thermal stability improving agent, after firing the coated layer, is usually incorporated in the alumina crystal structure. Since the amount of the thermal stability improving agent is however low and is not fixed, it is difficult to express the thermal stability improving agent-incorporated alumina by a compound having a particular composition.

The amount of the thermal stability improving agent based on the total weight of the alumina and the agent is preferably 0.05 to 8% by weight. If the amount is too low, the desired thermal stability improving effect is not obtained. If the amount is too high, the alumina may be deteriorated. 0.5 to 5% by weight is more preferable.

The catalyst for equilibrating an unburnt gas may comprise Pt, Rh, Pd, or a mixture thereof, with Pt/Pt being preferable.

The present invention is applicable to all types of oxygen concentration sensors, including the solid electrolyte type and resistance variable semiconductor type.

BRIEF EXPLANATION OF THE INVENTION

DESCRIPTION OF PREFERRED EMBODIMENTS

Figure 1:
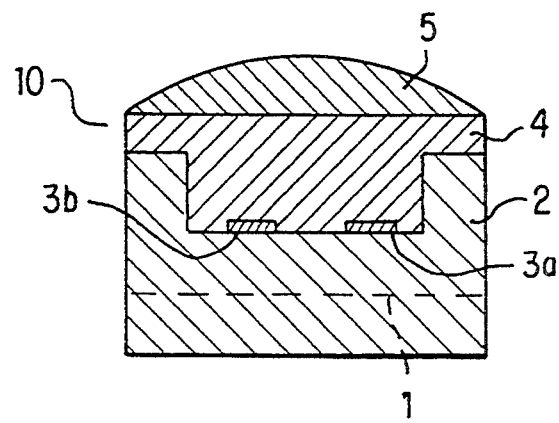
FIG. 1 is a cross-sectional view of an oxide semiconductor type oxygen sensor.

FIG. 1 shows an example of an oxide semiconductor type oxygen concentration sensor 10. The sensor 10 comprises a ceramic substrate 1 in which a heater 2 is embedded. The ceramic substrate 1 has a recessed portion on which electrodes 3a and 3b are formed and which is filled with an oxygen measuring layer 4 of an oxide semiconductor, for example, $TiO_2$. The heater 2 keeps the temperature of the oxygen measuring layer 4 to a predetermined temperature (oxygen gas reaction active temperature) of about 700° C. The oxygen measuring layer 4 carries a catalyst for accelerating an oxygen reaction there. The catalyst is usually identical to the catalyst carried on an alumina coating layer.

The top surface of the oxygen measuring layer 4 is covered with a porous coating layer 5 of alumina. The porous alumina coating layer 5 is porous in order to allow oxygen to reach the oxygen measuring layer 4, and traps oil components or the like in the exhaust gas. The porous alumina coating layer 5 also carries a catalyst of Pt/Rh for accelerating equilibration reaction of unburnt gases in the exhaust gas of an automobile. Here, the unburnt gases include hydrocarbons and/or carbon monoxide. The unburnt gases are equilibrated by the catalyst, for example, in the following chemical formula:

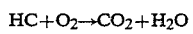

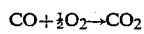

By this equilibration reaction, the unburnt gases are fully oxidized so that no unburnt gas remains and it is possible that an adequate oxygen concentration of the exhaust gas can be performed under the condition wherein the fuel (mainly hydrocarbons) is completely burnt with air (oxygen). The purpose of the oxygen concentration measurement is to detect the concentration of the excess oxygen in the burnt fuel gas exhausted from an engine when it is assumed that the fuel undergoes the ideal complete combustion. Accordingly, the remaining unburnt gases should be fully oxidized or equilibrated before the oxygen concentration is measured by the sensor. If the unburnt gas is not equilibrated, the desired and adequate excess oxygen concentration is not detected.

Figure 2:
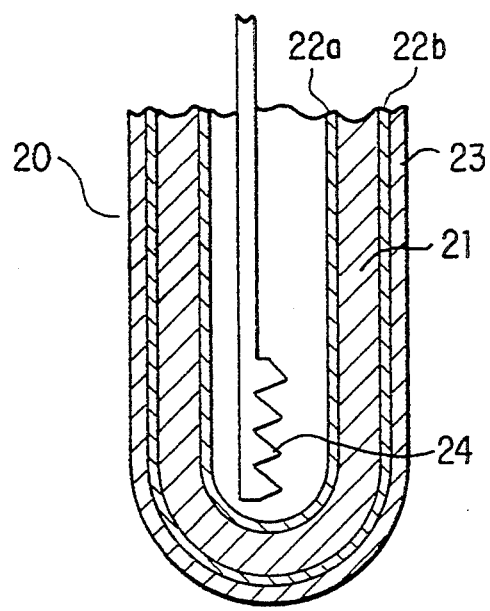
FIG. 2 is a cross section of an electrolyte type oxygen sensor.

FIG. 2 shows an example of a solid electrolyte type (zirconia) oxygen sensor 20. The sensor 20 comprises a zirconia layer 21 in the form of a cup, porous electrode layers 22a and 22b of Pt sandwiching the zirconia layer 21, a porous alumina coating layer 23 covering the outer electrode layer 22b, and a heater 24 inside the cup of the zirconia layer 21 and the inner electrode layer 22a.

The heater 24 keeps the temperature of the zirconia layer 21 to a predetermined temperature of about 400° to 700° C. The porous alumina coating layer 23 is porous so as to permeate oxygen to the zirconia layer 21. The porous alumina coating layer 23 traps oil components and so forth and carries a catalyst of Pt/Rh for accelerating the equalibration reaction of unburnt gases in the exhaust gas of an automobile.

The catalyst of Pt/Rh is carried on the porous alumina coating layer by dropwise applying a solution containing platinum chloride and rhodium chloride to the porous alumina coating layer or dipping the porous alumina coating layer in the solution, followed by heating the porous alumina layer so that the platinum and rhodium chlorides are reduced and platinum and rhodium are deposited on the porous alumina coating layer.

Figure 3A:
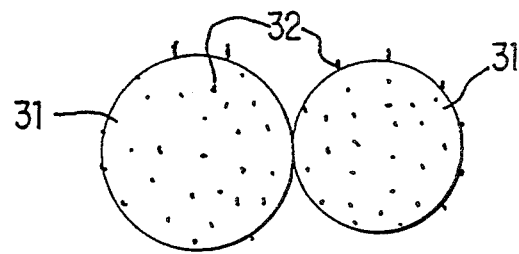
FIGS. 3A to 3C show the microstructure of a porous alumina coating layer on which a catalyst is carried.

FIG. 3A illustrates catalyst particles 32 of Pt/Rh deposited on alumina particles 31. As seen in FIG. 3A, the catalyst particles 32 are considerably fine, for example, about 1 to 50 nm diameter, while alumina particles 31 typically have diameters of about 1 to 4 $\mu$m. The amount of the catalyst is generally 3 to 4% by weight based on the weight of the alumina.

Figure 4:
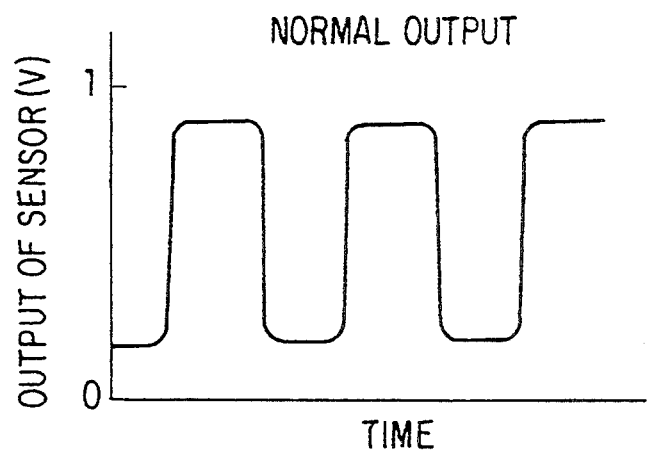
FIG. 4 shows the initial output characteristic of an oxygen sensor.
Figure 5:
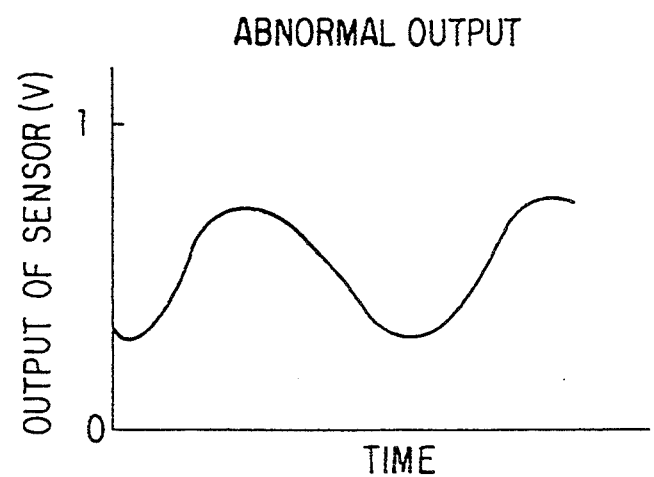
FIG. 5 shows the output characteristic of an oxygen sensor after a long time of use.

FIG. 4 shows the initial output characteristic of a sensor as described above, which is normal. Nevertheless, the output characteristic of the sensor becomes worse, i.e., abnormal, as shown in FIG. 5, when it is used for a considerably long time period. In FIG. 5, the output and response speed are lowered and the sensor does not work normally.

Figure 3B:
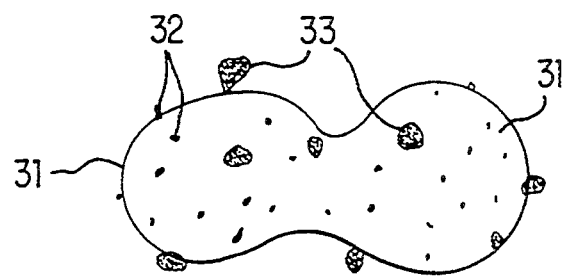

This abnormal output of the oxygen sensor is caused by cohesion of the catalyst particles 32 forming larger particles 33, as shown in FIG. 3B, by which the active surface area of the catalyst is decreased and the capability of equilibration is lowered.

The mechanism of accelerating the cohesion of the catalyst particles is considered as the following: Since the coating layer is exposed to the exhaust gas, the coating layer is usually heated to the temperature of the exhaust gas (300° to 850° C.). The temperature may reach 850° C. particularly in the cases of recent engines which are driven at a higher rotational speed. Moreover, the equilibration reaction of the unburnt gas in the coating layer is exothermic and the coating layer may be heated to above the temperature of the exhaust gas by the reaction. The heat causes the alumina particles to cohere and to grow in grain size. Due to and during this cohesion and grain growth of the alumina particles 31, the catalyst particles 32 carried on the alumina particles 31 are also cohere and grow in grain size.

Accordingly, if the cohesion and grain growth of the alumina particles 31 can be prevented, the cohesion and grain growth of the catalyst particles 32 can be also prevented and the catalyst activity can be maintained at a high level even after a long time use of the sensor.

Figure 3C:
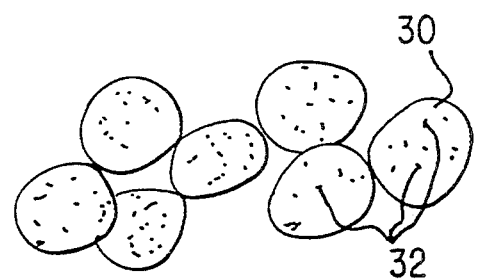

In accordance with the present invention, this prevention of the cohesion and grain growth of the alumina particles is attained by adding a thermal stability improving agent to alumina and firing the mixture, by which a stabilized alumina coating layer is formed. As a result, even after a long time use of the sensor for exhaust gas from automobile engines, the catalyst of Pt/Rh carried on the porous alumina coating layer remains fine, as shown in FIG. 3C, and does not lose its high activity as a catalyst. Thus, the life time of the oxygen sensor is prolonged in accordance with the present invention.

EXAMPLE

A titania-type oxygen concentration sensor as shown in FIG. 1 was fabricated. The structure was the same as that of a conventional one except that the porous alumina coating layer 5 contained a thermal stability improving agent.

More specifically, an alumina green sheet was prepared and cut into two sheets having the shape of the substrate 1. A heater pattern of platinum (Pt) was printed on one of the green sheets, electrodes patterns of Pt were printed on the other of the green sheets, and the latter green sheet was superimposed on the former green sheet. A further pattern of the alumina green sheet having the shape of the substrate 1 and a through hole was cut and superimposed on the already laminated green sheet patterns.

In the hole of the thus laminated alumina green sheets or the substrate 1, a titania (TiO$_2$) green sheet 4 was inserted to cover the electrode patterns 3a and 3b.

A coating slurry was prepared by milling 97 wt % of alumina powders ($\alpha$-alumina, average particle size of 4 $\mu$m) and 3 wt % of La$_2$O$_3$ powders (average particle size of about 0.1 $\mu$m) in a ball mill, adding an organic binder of polyvinylbutylal (PVB) and a solvent of isopropyl alcohol (IPA) into the ball mill, and milling the mixture again. The coating slurry was coated on the titania green sheet 4.

The thus formed laminate was fired in air at 1150° C. for 2 to 5 hours to obtain a sintered body of an oxygen concentration sensor.

The alumina coating layer 5 and titania oxygen measuring layer 4 of the sintered body was porous, on which a Pt/Rh catalyst may be carried by a known method. For example, an aqueous solution containing platinum chloride and rhodium chloride were dropwise applied to the coating layer followed by heating so that the Pt and Rh chlorides were reduced to deposit Pt and Rh on the titania and alumina particles of the titania oxygen measuring layer 4 and porous alumina coating layer 5.

Thus, an oxygen concentration sensor containing La$_2$O$_3$ (thermal stability improving agent) in alumina coating and carrying a catalyst was prepared.

This oxygen concentration sensor was subjected to a high temperature durability test in which the sensor was mounted to a model system with an automobile engine, the engine was driven for a 120,000 mile drive, and the temperature of the exhaust gas near the sensor was 850° C. After this test, the output characteristic of the oxygen concentration sensor was normal as shown in FIG. 4 and was not changed from its initial output characteristic. Further, the La$_2$O$_3$-containing alumina particles were hardly cohered and grown in their grain size and the catalyst was widely distributed as fine particles without cohesion of the particles.

Similar effects were obtained when La$_2$O$_3$ was replaced by a rare earth element oxide other than La$_2$O$_3$, such as SiO$_2$, MgO, BaO, CaO or an alkali metal oxide.

In contrast, when no thermal stability improving agent was added to alumina, the output characteristic of the sensor was deteriorated and became abnormal as shown in FIG. 5 after the same high temperature durability test for the time corresponding to 12,000 miles drive.

Furthermore, when a thermal stability improving agent is added, the capability of equilibration is improved by a rare earth element oxide and the oxidation reaction of hydrocarbon is accelerated particularly by $La_2O_3$.

I claim:

1. An oxygen concentration sensor comprising a sensor body and a porous ceramic coating layer carrying a catalyst for equilibrating an unburnt gas, the porous ceramic coating layer being formed on the sensor body, wherein said porous ceramic coating layer is made of a material formed by firing a mixture of alpha alumina powder having an average particle size of four microns with 0.05 to 8% by weight of a thermal stability improving agent powder that inhibits grain growth in the porous ceramic coating layer, the thermal stability improving agent having an average particle size of 0.1 microns.

2. An oxygen concentration sensor according to claim 1, wherein said thermal stability improving agent is at least one oxide selected from the group consisting of rare earth element oxides, $SiO_2$, MgO, BaO, CaO, and alkali metal oxides.

3. An oxygen concentration sensor according to claim 1, wherein said sensor body comprises a solid electrolyte, electrodes and a heater.

4. An oxygen concentration sensor according to claim 1, wherein said sensor body comprises a semiconductor, the electrical resistance of which is varied depending on the concentration of oxygen in contact with the semiconductor, electrodes and a heater.

5. An oxygen concentration sensor according to claim 1, wherein said catalyst comprises platinum and rhodium.

6. An oxygen concentration sensor according to claim 1, wherein the thermal stability improving agent prevents grain growth of catalyst particles in the porous ceramic coating layer caused by heat.

7. An oxygen concentration sensor, comprising:
a heating element;
a solid electrolyte layer formed around the heating element and sandwiched between first and second porous electrode layers, the first porous electrode layer being formed between the electrolyte layer and the heating element, the second electrode layer being formed on the electrolyte layer on a side opposite the first electrode layer; and
a porous coating layer formed on the second electrode layer, the porous coating layer comprising alpha alumina particles having an average particle size of 4 microns, catalyst particles, and a thermal stability improving agent that has an average particle size of 0.1 microns inhibits grain growth of the alpha alumina particles due to heat.

8. The device of claim 7, wherein the thermal stability improving agent comprises between approximately 0.05 and approximately 8 percent by weight of the porous coating layer.

9. The device of claim 7, wherein the thermal stability improving agent comprises a material selected from the group consisting of rare earth element oxides, $SiO_2$, MgO, BaO, CaO, and alkali metal oxides.

10. The device of claim 9, wherein the thermal stability improving agent comprises between approximately 0.05 and approximately 8 percent by weight of the porous coating layer.

11. The device of claim 7, wherein the thermal stability improving agent inhibits grain growth of the catalyst particles due to heat.

12. The device of claim 7, wherein the catalyst particles comprise at least one of platinum, rhodium, and palladium.

13. An oxygen concentration sensor, comprising:
a ceramic substrate;
a heating element attached to the substrate;
first and second electrodes attached to the substrate;
an oxygen measuring oxide semiconductor layer formed over and between said first and second electrodes, the resistance of the oxide semiconductor layer varying depending on the concentration of oxygen in contact with the oxide semiconductor layer so that the electrical resistance between the first and second electrodes provides an indication of the concentration of oxygen in contact with the oxide semiconductor layer; and
a porous coating layer formed over the oxide semiconductor layer, the porous coating layer comprising alpha alumina particles having an average particle size of 4 microns, catalyst particles, and a thermal stability improving agent that has an average particle size of 0.1 microns inhibits grain growth of the alpha alumina particles.

14. The device of claim 13, wherein the thermal stability improving agent comprises between approximately 0.05 and approximately 8 percent by weight of the porous coating layer.

15. The device of claim 13, wherein the thermal stability improving agent comprises a material selected from the group consisting of rare earth element oxides, $SiO_2$, MgO, BaO, CaO, and alkali metal oxides.

16. The device of claim 15, wherein the thermal stability improving agent comprises between approximately 0.05 and approximately 8 percent by weight of the porous coating layer.

17. The device of claim 13, wherein the thermal stability improving agent inhibits grain growth of the catalyst particles due to heat.

18. The device of claim 13, wherein the catalyst particles comprise at least one of platinum, rhodium, and palladium.

19. The device of claim 13, wherein the oxide semiconductor layer further comprises a catalyst comprised of at least one of platinum, rhodium, and palladium.

* * * * *